(12) United States Patent
Frye

(10) Patent No.: US 7,794,304 B2
(45) Date of Patent: Sep. 14, 2010

(54) COMFORT BRA LINER

(76) Inventor: Donna J. Frye, 26491 Merienda #1, Laguna Hills, CA (US) 92656

( * ) Notice: Subject to any disclaimer, the term of this patent is extended or adjusted under 35 U.S.C. 154(b) by 95 days.

(21) Appl. No.: 12/257,975

(22) Filed: Oct. 24, 2008

(65) Prior Publication Data

US 2010/0101585 A1    Apr. 29, 2010

(51) Int. Cl.
    *A41C 3/00* (2006.01)
(52) U.S. Cl. ................... 450/37; 450/81; 2/53
(58) Field of Classification Search .............. 450/36, 450/37, 54–58, 1, 81; 2/267, 268, 46, 53, 2/56, 57, 455, 463, 50, 60
    See application file for complete search history.

(56) References Cited

U.S. PATENT DOCUMENTS

| 2,534,721 | A | * | 12/1950 | Marshall | 450/36 |
| 2,641,763 | A | | 6/1953 | Schroeder | |
| 2,863,460 | A | * | 12/1958 | Monroe | 450/11 |
| 2,869,552 | A | * | 1/1959 | Smith | 450/32 |
| 5,573,441 | A | * | 11/1996 | Smith | 450/89 |
| 5,980,359 | A | * | 11/1999 | Brown | 450/57 |
| 5,996,120 | A | | 12/1999 | Balit | |
| 6,203,399 | B1 | * | 3/2001 | Hackney | 450/1 |
| 6,264,530 | B1 | * | 7/2001 | Cosentino | 450/57 |
| 7,201,629 | B2 | * | 4/2007 | Lambru | 450/1 |
| 7,585,200 | B1 | * | 9/2009 | McLaren | 450/89 |

OTHER PUBLICATIONS

Webpage; www.pambras.com/3252.html; "What is Pambra's, The Original Bra Liner?" (2 pages).
Webpage; http://www.amazon.com/Single-Try-Absorbing-Comfortable-S-M-L-XL-XXL/dp/B002MHZo6Y/ref=pd_sbs_a_1; "Absorbing Comfortable White Bra Liner" (4 pages).
Webpage; http://www.amerimark.com/cgi-bin/amerimark/prod/22351/item_detail.html?keywords=bra%20liner&srcmode=&sortbyprice=; "Bra Liners" (1 page).
Webpage; http://bramates.com/?gclid=CPu4j4LQiJ0CFRyenAod1ha7bg; "BraMates Bra Liners" (2 pages).
Webpage; http://www.comforthouse.com/bralin.html; "Absorbent Bra Liners Keep You Dry" (2 pages).
Webpage; http://www.amazon.com/3-Pack-Absorbing-Comfortable-Liners-Sizes/dp/B0023XCKAA; "3-Pack Absorbing n' Comfortable Bra Liners" (5 pages).

* cited by examiner

*Primary Examiner*—Gloria Hale
(74) *Attorney, Agent, or Firm*—Stetina Brunda Garred & Brucker

(57) ABSTRACT

A foldable one-piece insert worn between the bra and the body having irritation reducing and/or absorbent material portions which line the bra cup and that lie under the supported breast, and portions which extends toward the torso rear under the bra side straps and a portion extending below the bra line along the torso. The invention further includes a material tab disposed between the material portions lining the bra cups, which can optionally be worn up to bridge the area between the bra cups for added protection, comfort and absorption of perspiration, or be folded down and out of sight when worn with lower cut neckline outer garments.

18 Claims, 2 Drawing Sheets

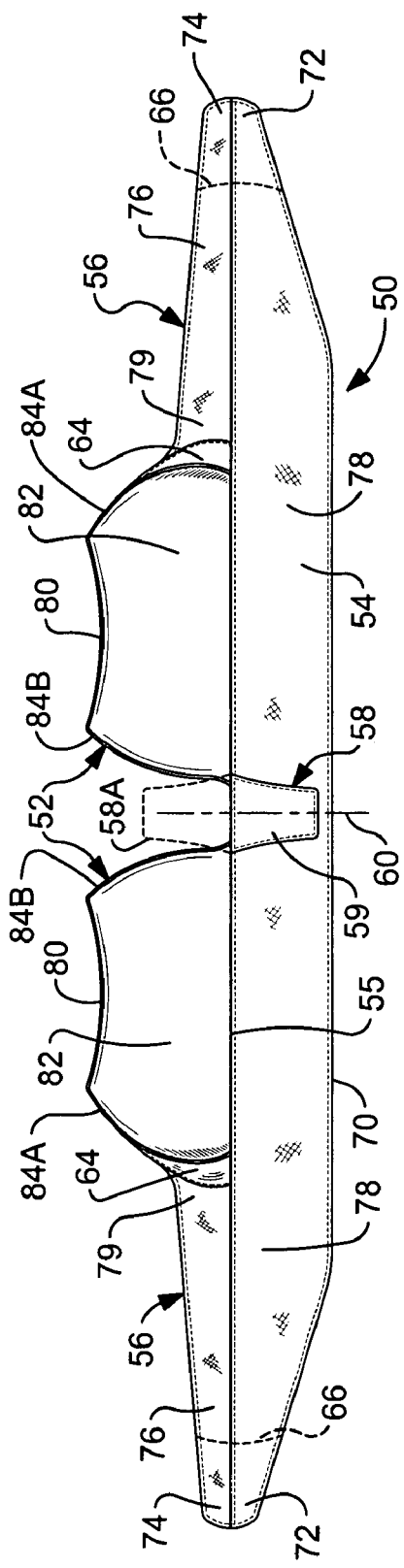
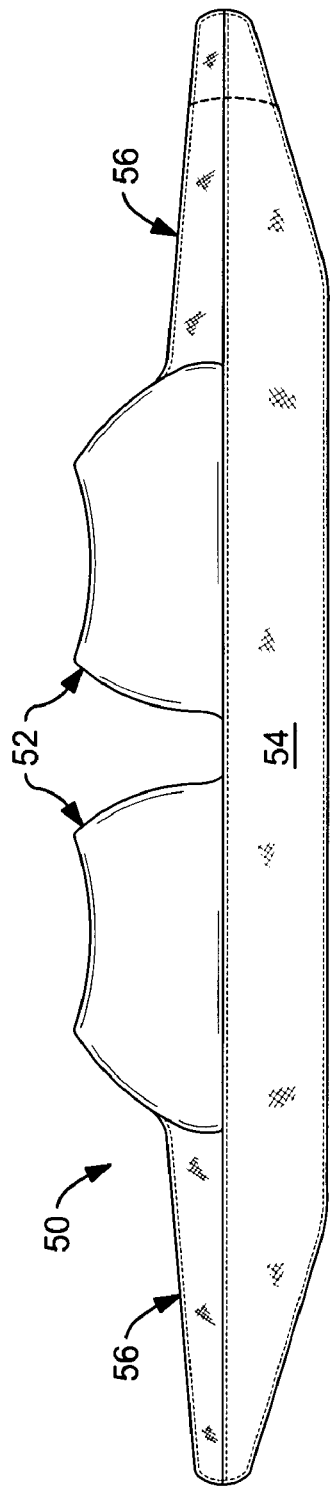

COMFORT BRA LINER

FIELD OF THE INVENTION

The present invention relates to bra liners, in particular to bra liners having a contoured profile to provide selective contact with the body when used with conventional bras.

BACKGROUND OF THE INVENTION

Wearers of bras experience sores, rashes, skin tags and irritation under the breast resulting from perspiration and skin-to-skin contact. Furthermore, conventional bra construction offers little to address this problem area, having a material or construction which are designed for esthetic concerns. Additional discomfort arises in areas under the bra peripherally related to the breast such as under the side straps, and in areas adjacent to the bra, such as immediately below the bra line along the torso.

SUMMARY OF THE INVENTION

The bra liner according to the present invention provides a foldable one-piece insert worn between the bra and the body having irritation reducing or absorbent material portions which line the bra cup and that lie under the supported breast, and portions which extends toward the torso rear under the bra side straps, and a portion extending below the bra line along the torso.

A further feature includes a material tab disposed between the bra cup liners which can optionally be worn up to bridge the area between the bra cups for added protection, comfort and absorption of perspiration, or be folded down and out of sight when worn with lower cut neckline outer garments.

A still further feature according to the present invention provides removable inserts which are retained within the bra cup by material associated with the bra cup liner to help prevent dislocation of the inserts, which may comprise additional irritation reducing or absorbent material which may be desirable for comfort after surgery or exercise. Inserts also include appropriately shaped structures which provide lift, support, protection or esthetic enhancement.

A still further feature includes a curved front edge of the cup liner portions which are shaped to lie under the breast while avoiding contact with the breast nipple and areola areas to reduce of potential irritation and allow convenient breast feeding.

When worn, the bra liner according to one aspect of the present invention is foldable with one portion including the cup liners being placed in the bra cups, and a second portion which is unfolded and placed below the bra under the bra cups. Additional members extend from the cup liners and are placed between the bra straps and the wearer. The bra liner may be adjusted by the wearer to separate skin-to-skin contact and otherwise positioned between the bra and the torso for the desired comfort and/or absorption not possible with the bra. While worn, the material tab between the cup liners may be revealed by folding up, between the bra cups, or down, and inserts may be added or removed as desired.

BRIEF DESCRIPTION OF THE DRAWINGS

Various objects, features, and attendant advantages of the present invention will become more fully appreciated as the same become better understood when considered in conjunction with the accompanying drawings, in which like reference characters designate the same or similar part throughout the several view, and wherein:

FIG. 1 is a rear elevation view of one embodiment of the present invention;

FIG. 2 is a front elevation view of the embodiment of FIG. 1;

DETAILED DESCRIPTION

Figure 3:
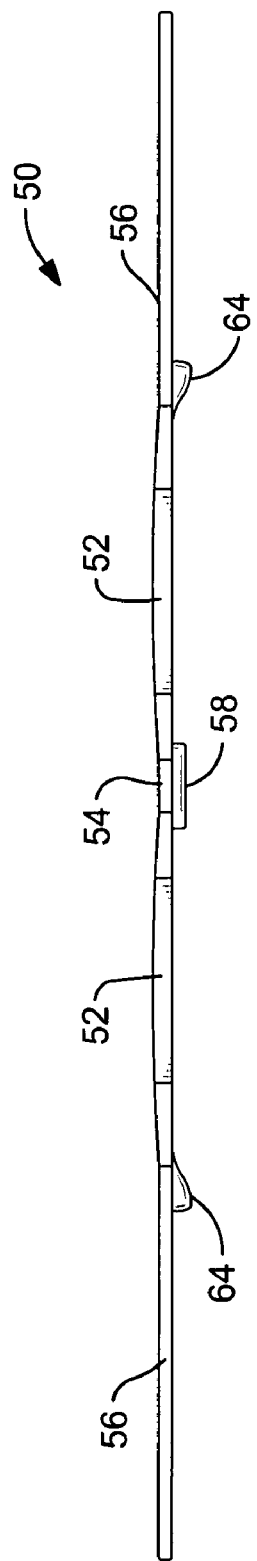
FIG. 3 is a plan view of the embodiment of FIG. 1.

With the construction of a typical bra being understood, an exemplary embodiment 50 according to the present invention is shown in FIG. 1-3, including cup liners 52 which the wearer inserts into the bra and places under the breast, is attached to a strip 54 which retains the cup liners 52 in relative position and generally symmetrically outward from a midline 60, and when worn extends at least partially below the bra to be generally disposed over and at least partially in contact the body adjacent to the breast area to provide additional comfort and/or absorption in that area as well. The exemplary bra liner 50 further includes material bands 56 extending from the cup liner 52 parallel and include edges 76 connected to the edge 78 of strip 54 toward the ends thereof to form a foldable seam 55 with an opposing edge 70.

In the exemplary embodiment 50, both the bands 56 and the strip 54 have outer ends 74 and 72 respectively, terminating at substantially the same distance from the midline 60, but alternate embodiments may have either band(s) 56 or strip 54 extend farther. Typically, the bands 56 extend at least partially under the bra side straps (not shown) when in use. Furthermore, for applications where the bra liner 50 is to be worn to more completely encircle the body of the wearer, at least the bands 56 (and optionally the ends 72 of strip 54) can extended further along the bra straps to extend further around the torso of the wearer, and in some embodiments, touch or overlap each other. Alternately, embodiments having a shorter terminus 66 of the bands 56 and/or strip 54 may be provided.

The cup liners 52 typically each have an arcuate edge 80 substantially opposite the edge 82 which edge 82 joins the strip 54 at seam 55, and further that arcuate edge 80 is generally shorter than edge 82 comprising material shaped or sufficiently pliant to conform to the bra cup when worn by the wearer. The edges 80 and 82 are connected by outer side 84A and inner side 84B, which are shaped to conform to provide the desired function as described above. The outer sides 84A are typically connected to the inner ends 79 of bands 56. The specific dimensions of the cup liner width between edges 80 and 82, as well as the shape or radius of the arcuate edge 80 is scaled according to the size of the wearer and corresponding bra, and dimensioned to substantially avoid contact with the breast nipple and if desired, the areola as well when placed in the bra.

A material tab 58 as shown in FIG. 1, has an edge 59 connected to the strip 54 edge 78 and is foldable thereon from a 'down' position as shown overlaying the strip 54, to an 'up' position 58A where it at least partially overlaps the cup insert 52 inner edges 84B. In the exemplary embodiment shown, the cup inserts are separated with an intervening space between inner edges 84A, and the present embodiment bridges at least a portion of that space. The tab 58 may be pulled up (58A) for protection, absorption and comfort as needed.

Figure 4:
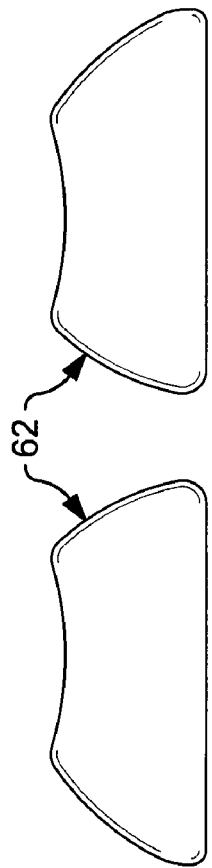
FIG. 4 is an elevation view of exemplary inserts as may be applied to the embodiment of FIG. 1.

Exemplary inserts 62, as shown in FIG. 4, may be applied to the present invention, and by reference to the exemplary embodiment 50 of FIGS. 1-3, generally retained on the cup liner 52 with optional flaps 64 shown in FIG. 1, which flaps 64 have outer edges connected to the cup liner outer edges 84A and lower edges connected to the cup liner 52 lower edge 82 to form a pouch to receive an edge, side, end, margin or other portion of the inserts 62 when worn by the wearer. The inserts are selected by the wearer to provide additional protection, to reduce irritation, to enhance absorption, to provide support, lift, and esthetic improvement (including prosthesis) as desired.

The material used in the embodiments of the present invention in its entirety or individual component members thereof, may comprise irritation mitigating material, perspiration or fluid absorbent material, elastic material, padding, and other material sufficient to provide the embodiments described above. Particular material such as cotton, cotton blends and organic or non-allergenic material may be used for all or portions of the various embodiments of the present invention.

The embodiments according to the present invention may provide different sizing from small to extra large, and offer extended length to accommodate users who wish to extend the bra liner to farther under the bra side straps to extend to the back of the torso. Further embodiments are adapted for use with nursing bras that may be used in accordance with the opening afforded by the front edge of the cup liner portion. Further modifications and substitutions made by one skilled in the art are within the scope of the present invention which is not to be limited except by the claims which follow.

What is claimed is:

1. A bra liner for use under a bra, the bra having a strap with cups attached thereto for supporting breasts of a wearer, the liner comprising:

an elongate strip of thin material disposable under the strap, the strip defining a length defined by opposing end portions, a middle portion between the opposing end portions, opposing upper and lower edge portions and a width defined by the opposing upper and lower edge portions, the length of the strip being greater than the width of the strip;

a pair of cup liners disposable under the cups of the bra, the cup liners having a length, a bottom edge portion, and an arcuate concave top edge portion opposite from the bottom edge portion, the bottom edge portion attached to the upper edge portion of the strip, the pair of cup liners disposed substantially symmetrically outward from the middle portion of the strip, the pair of cup liners each having a width between the bottom edge portion and the arcuate top edge portion, the arcuate top edge portion having a longitudinal dimension less than a longitudinal dimension of the bottom edge portion, wherein the top and bottom edge portions are each connected by opposing inner and outer edge portions, the inner edge portions of each of the cup liners are proximal the middle portion, a pair of parallel bands each having inner and outer end portions and a length therebetween which is greater than a width of the parallel bands, the parallel bands being attached to the upper edge portion of the strip wherein the outer end portion of each band is proximal to an outer end portion of the strip and each inner end portion is connected to the outer edge portion of a corresponding one of the pair of cup liners; and a tab having an edge portion joined to the strip upper edge portion, partially overlapping the cup liners inner edge portion, and foldable away from the cup liners first edges and toward the strip lower edge portion.

2. The bra liner of claim 1, further comprising a pair of flaps, each flap attached to said upper edge portion of said strip and to said second end portion of a corresponding one of said pair of cup liners together with said corresponding one of said pair of cup liners forming a pocket.

3. The bra liner of claim 2, further comprising an insert disposed at least partially within the cup liner pocket.

4. The bra liner of claim 1, wherein at least one of said strip and said bands has a diminished width distal from said middle portion.

5. The bra liner of claim 1, wherein at least one of said strip, cup liner, band, tab and flap comprises an absorbent material.

6. The bra liner of claim 1, wherein the width of the cup liner is less than the length of the cup liner.

7. The bra liner of claim 1, wherein said cup liners comprise an arcuate convex edge.

8. The bra liner of claim 1, further including a foldable seam thereon.

9. A bra liner for a bra, the bra defining cups, comprising:
a pair of cup liners disposable between the cups of the bra and the wearer;
a strip defining an upper edge portion and a lower edge portion, the pair of cup liners attached to the upper edge portion of the strip, the pair of cup liners spaced away from each other on the upper edge portion of the strip; and
a foldable tab connected to the upper edge portion of the strip and disposed between the cup liners, the tab having an upright position to overlay the space between the cup liners and a folded position to open the space between the cup liners.

10. The bra liner of claim 9, further including
a pair of absorbent inserts, and
a pair of insert pockets formed on the cup liners, the inserts disposable within the insert pockets.

11. The bra liner of claim 9, wherein the strip and the cup liners are fabricated from a fluid absorbent material or wicking material.

12. A bra liner for use between a bra and a wearer thereof wherein said bra includes at least one cup and at least one strap encircling the torso of said wearer, the strap defining a bra line, the bra liner comprising:
a first cup liner fitted under said cup;
a strip fitted at least partially under said strap and attached to said first cup liner; and
a liner extension attached to said strip member and extending below said bra line.

13. The bra liner of claim 12, further including an insert retainer peripherally attached to said first cup liner forming a pouch with said first cup liner.

14. The bra liner of claim 12, further including an insert disposed within said pouch formed by said insert retainer.

15. The bra liner of claim 12, wherein said strip comprises a strip having a length sufficient to encircle said torso.

16. The bra liner of claim 12, further comprising a second cup liner attached to said strip member and spaced a selected distance from said first cup liner, and a tab attached to said strip and foldable between a folded position and an unfolded position, in the unfolded position, the tab covers at least a portion of said selected distance between said first and said second cup liner, in the folded position, the tab is folded away from the space between the cup liners.

17. A bra liner fittable under a bra worn by a person, the liner comprising:
an elongate strip of thin material disposable between a strap of the bra and the wearer, the elongate strip defining an upper edge portion;
left and right cup liners disposable between left and right cups of the bra and attached to the upper edge portion of the strip, upper edge portions of the cup liners having a concave configuration so that the cup liners avoid contact with the breast nipples of the person.

18. The liner of claim 17 wherein the concave configuration of the upper edge portions of the cup liners are sufficient to avoid contact with the areola of the person.

* * * * *